United States Patent
Wang et al.

(10) Patent No.: US 12,390,503 B2
(45) Date of Patent: Aug. 19, 2025

(54) GINKGO BILOBA LEAVE EXTRACT CAPSULE AND PREPARATION METHOD THEREFOR

(71) Applicant: SPH XING LING SCI. & TECH. PHARMACEUTICAL CO., LTD., Shanghai (CN)

(72) Inventors: Dandan Wang, Shanghai (CN); Qi Gao, Shanghai (CN); Jun Wang, Shanghai (CN); Baozhong Zhu, Shanghai (CN); Cunfa Li, Shanghai (CN); Xueyi Zhang, Shanghai (CN); Yafang Wei, Shanghai (CN)

(73) Assignee: SPH XING LING SCI. & TECH. PHARMACEUTICAL CO., LTD., Shanghai (CN)

( * ) Notice: Subject to any disclaimer, the term of this patent is extended or adjusted under 35 U.S.C. 154(b) by 1216 days.

(21) Appl. No.: 17/264,152

(22) PCT Filed: Sep. 12, 2018

(86) PCT No.: PCT/CN2018/105256
§ 371 (c)(1),
(2) Date: Aug. 24, 2021

(87) PCT Pub. No.: WO2020/037736
PCT Pub. Date: Feb. 27, 2020

(65) Prior Publication Data
US 2022/0080005 A1 Mar. 17, 2022

(30) Foreign Application Priority Data
Aug. 20, 2018 (CN) .......................... 201810945350.3

(51) Int. Cl.
*A61K 36/16* (2006.01)
*A61K 9/48* (2006.01)
*A61K 31/365* (2006.01)

(52) U.S. Cl.
CPC ............... *A61K 36/16* (2013.01); *A61K 9/48* (2013.01); *A61K 9/4858* (2013.01); *A61K 9/4866* (2013.01); *A61K 31/365* (2013.01)

(58) Field of Classification Search
None
See application file for complete search history.

(56) References Cited

U.S. PATENT DOCUMENTS

| 5,389,370 A | 2/1995 | O'Reilly et al. |
| 5,399,348 A | 3/1995 | Schwabe |
| 2009/0238902 A1* | 9/2009 | Liu ...................... A61K 9/1652 |
| | | 424/728 |

FOREIGN PATENT DOCUMENTS

| CN | 1508542 A | 6/2004 |
| CN | 1977868 A | 6/2007 |
| CN | IO1628003 A | 1/2010 |
| CN | 104306371 A * | 1/2015 | ........... A61K 31/365 |
| CN | IO6420849 A | 2/2017 |
| EP | 1964551 A1 * | 9/2008 | ........... A61K 31/122 |

OTHER PUBLICATIONS

Google translation CN 104306371 A, printed 2024 (Year: 2024).*
CN 104257634 A, published Jan. 7, 2015, USPTO translation and original document (Year: 2015).*
Google translation CN 104257634 A, printed 2024 (Year: 2024).*
CN 101628003 A, published Jan. 20, 2010, USPTO translation and original document (Year: 2010).*
Google translation CN 101628003 A, printed 2024 (Year: 2024).*
CN 104398543 A, published Mar. 11, 2015, USPTO translation and original document (Year: 2015).*
Google translation, CN 104398543 A, printed 2024 (Year: 2024).*

* cited by examiner

*Primary Examiner* — Marianne C Seidel
*Assistant Examiner* — Alissa Prosser
(74) *Attorney, Agent, or Firm* — IPRTOP LLC

(57) ABSTRACT

The present disclosure provides a ginkgo biloba ketone ester capsule. The present disclosure further provides a method for preparing ginkgo biloba ketone ester capsule and use thereof. The present disclosure provides a ginkgo biloba ketone ester capsule and a preparation method thereof. Through optimized preparation operations and conditions, a high-quality ginkgo biloba ketone ester capsule can be obtained. Compared with the ginkgo biloba ketone ester capsule prepared by traditional methods, the ginkgo biloba ketone ester capsule of the present disclosure has stable quality and a low unqualified rate. The consistency of different batches of ginkgo biloba ketone ester capsules is good. In particular, the ginkgo biloba ketone ester capsule can effectively control ginkgolic acids, preventing the use of high-ginkgolic-acid raw materials in the ginkgo biloba ketone ester capsules, so as to effectively improve the safety of ginkgo biloba ketone ester capsules.

5 Claims, 1 Drawing Sheet

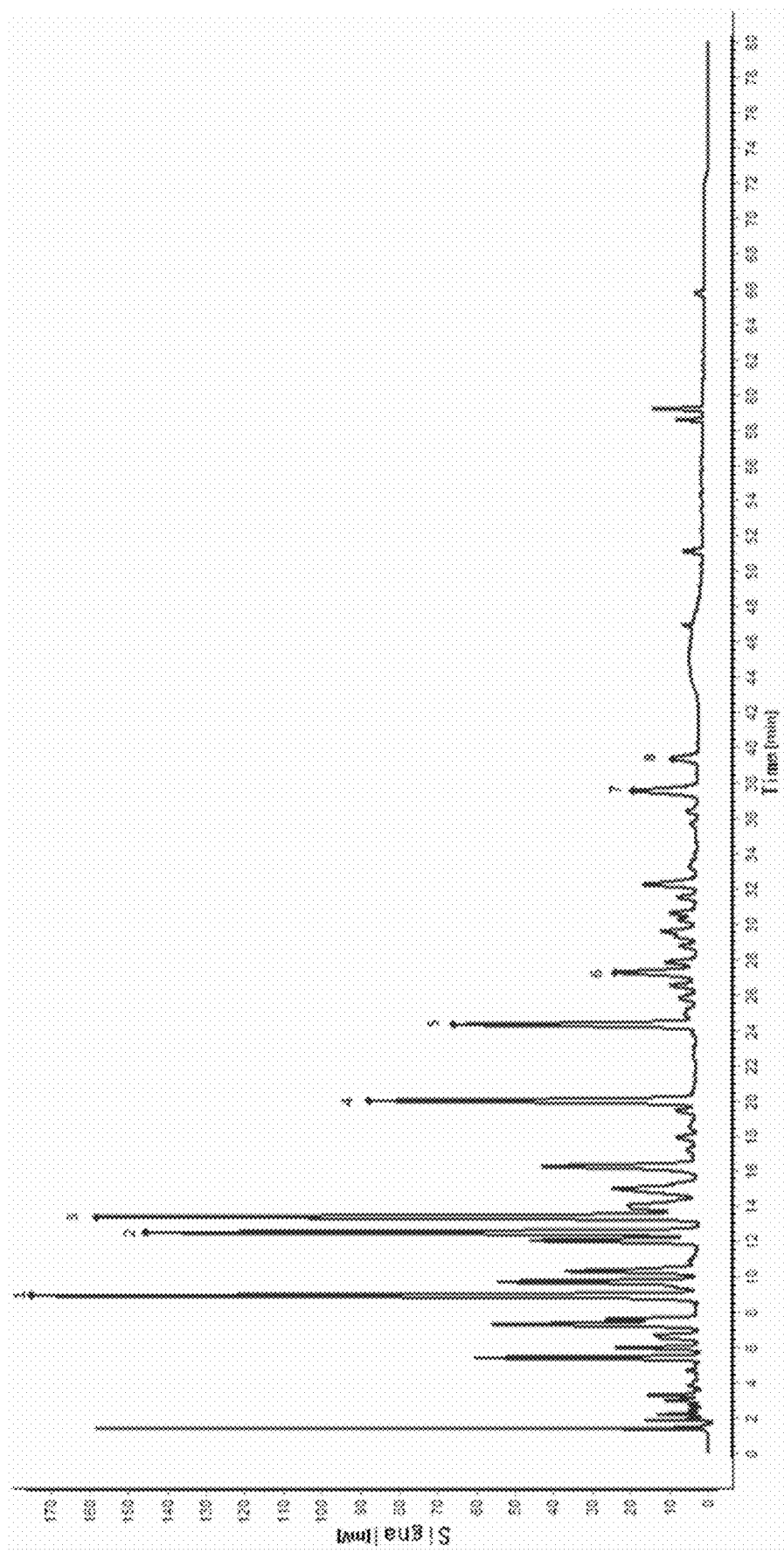

GINKGO BILOBA LEAVE EXTRACT CAPSULE AND PREPARATION METHOD THEREFOR

TECHNICAL FIELD

The disclosure relates to the technical field of traditional Chinese medicines, and in particular, to a ginkgo biloba ketone ester capsule and preparation method thereof

BACKGROUND

With the increasing aging of the population in China, people's awareness of prevention and treatment of cardiovascular and cerebrovascular diseases is gradually increasing. Ginkgo biloba leaves are the dry leaves of Ginkgo biloba which are sweet, bitter, astringent and calming, and belongs to heart and lung channels. According to the records of "Chinese Traditional Medicine Records", ginkgo biloba leaves can "astringe Lung Qi, relieve cough and asthma, and stop whites and turbidity". Ginkgo biloba ketone ester is a ginkgo biloba extract product developed in China. It is an extract from the dried leaves of Ginkgo Biloba L, a plant of the Ginkgo family. Ginkgo biloba ketone ester includes various forms of preparations. Among those preparations, ginkgo biloba ketone ester capsules are hard capsules. The contents of ginkgo biloba ketone ester capsules are light-yellow to brown granules and powder. Meanwhile, ginkgo biloba ketone ester capsules have a mild scent and taste a little bitter. Ginkgo biloba ketone ester capsules are mainly used in the treatment of dizziness, coronary heart disease and angina pectoris caused by blood-stasis-type chest obstruction and blood-stasis-type mild cerebral arteriosclerosis as well as in blood-activating and stasis-eliminating, and the curative effect is remarkable. Due to the remarkable curative effect of ginkgo biloba ketone ester capsules, adulteration is serious in the production process of relevant products on the market. For example, flavonoid aglycones such as quercetin are added to significantly increase the detected content of total flavonol glycosides, which superficially meets the technical requirements of ginkgo biloba ketone ester capsules but actually affects the internal quality of the drug products. Meanwhile, the content of ginkgolic acids in related products on the market has not been effectively controlled. Raw materials with high ginkgolic acids are added, which causes a certain safety risk. However, traditional preparation methods and quality standards have limitations, which are difficult to ensure the quality stability of ginkgo biloba ketone ester capsules, resulting in a high unqualified rate of ginkgo biloba ketone ester capsules. In order to ensure the consistency of different batches of ginkgo biloba ketone ester capsules, further research and discussion on ginkgo biloba ketone ester capsules are needed.

SUMMARY

The present disclosure provides a ginkgo biloba ketone ester capsule and preparation method thereof, to solve the problem that the traditional ginkgo biloba ketone ester capsule is unstable in quality and low in qualification rate.

The first aspect of the present disclosure provides a ginkgo biloba ketone ester capsule, which is prepared by mixing ginkgo biloba ketone ester raw materials and excipients, granulating and filling into capsules. The ginkgo biloba ketone ester capsules, based on the loading weight of each capsule 0.2 g, meet the following conditions:

1) the content of rutin ($C_{27}H_{30}O_{16}$, CAS number 153-18-4) is less than or equal to 1.60 mg/capsule;
2) the content of quercetin ($C_{15}H_{10}O_7$, CAS number 117-39-5) is less than or equal to 0.160 mg/capsule;
3) the content of bilobalide ($C_{15}H_{18}O_8$, CAS number 33570-04-6) is 1.04-2.08 mg/capsule;
4) the content of ginkgolide J ($C_{20}H_{24}O_{10}$, CAS number 107438-79-9) is 0.04-0.20 mg/capsule;
5) the residual content of ethanol is less than or equal to 0.2 mg/capsule;
6) the content of biflavonoids is less than or equal to 0.008 mg/capsule, the biflavonoids include Amentoflavone ($C_{30}H_{18}O_{10}$, CAS number 1617-53-4), Bilobetin ($C_{31}H_{20}O_{10}$, CAS number: 521-32-4), and Ginkgetin ($C_{32}H_{22}O_{10}$, CAS number 481-46-9);
7) the content of Genistin (CAS number 529-59-9) is 0, and the content of ginkgolide M (CAS number 15291-78-8) is 0.

Preferably, the content of the rutin is less than or equal to 1.28 mg/capsule.

Preferably, the content of the quercetin is less than or equal to 0.152 mg/capsule.

Preferably, the residual content of ethanol is less than or equal to 0.08 mg/capsule.

Preferably, the content of the bilobalide is 1.44-1.92 mg/capsule.

Preferably, the content of the ginkgolide J is 0.12-0.20 mg/capsule.

Preferably, the content of the biflavonoids is less than or equal to 0.004 mg/capsule.

Preferably, the content of total flavonoids in the ginkgo biloba ketone ester capsule is 14.08-26.40 mg/capsule by using rutin ($C_{27}H_{30}O_{16}$) as a standard sample.

More preferably, the content of total flavonoids in the ginkgo biloba ketone ester capsule is 17.6-22 mg/capsule by using rutin as a standard sample.

Further preferably, the content of total flavonoids in the ginkgo biloba ketone ester capsule is 19.6-22 mg/capsule by using rutin as a standard sample. The content of total flavonoids in the ginkgo biloba ketone ester capsule is calculated according to General Rules 0401 in Chinese Pharmacopoeia (2015 Edition) Volume IV.

Preferably, the content of terpene lactones in the ginkgo biloba ketone ester capsule is 2.4-4.8 mg/capsule calculated by the total contents of bilobalide ($C_{15}H_{18}O_8$, CAS number 33570-04-6), ginkgolide A ($C_{20}H_{24}O_9$, CAS number 15291-75-5), ginkgolide B ($C_{20}H_{24}O_{10}$, CAS number 15291-77-7) and ginkgolide C ($C_{20}H_{24}O_{11}$, CAS number 15291-76-6). The content of terpene lactones is calculated as dry products.

More preferably, the content of terpene lactones in the ginkgo biloba ketone ester capsule is 3.6-4.8 mg/capsule calculated by the total contents of bilobalide, ginkgolide A, ginkgolide B and ginkgolide C.

Preferably, the content of total ginkgolic acids in the ginkgo biloba ketone ester capsule is less than or equal to 2 μg/capsule.

More preferably, the content of total ginkgolic acid in the ginkgo biloba ketone ester capsule is less than or equal to 1 μg/capsule.

More preferably, the total ginkgolic acids in the ginkgo biloba ketone ester capsule are characterized by the total content of ginkgolic acid C13:0 ($C_{20}H_{32}O_3$, CAS number 20261-38-5), ginkgolic acid C15:1 ($C_{22}H_{34}O_3$, CAS number 22910-60-7), and ginkgolic acid C17:1 ($C_{24}H_{38}O_3$, CAS number 111047-30-4). The content of total ginkgolic acids is calculated according to General Rules 0512 and 0431 in Chinese Pharmacopoeia (2015 Edition) Volume IV.

Preferably, the content of total flavonol glycosides in the ginkgo biloba ketone ester capsule is 9.6-14.0 mg/capsule. The content of total flavonol glycosides is calculated as dry products.

More preferably, the content of total flavonol glycosides in the ginkgo biloba ketone ester capsule is 12.0-14.0 mg/capsule.

More preferably, the total flavonol glycosides are mainly glycosides formed by quercetin, kaempferide and isorhamnetin as aglycons, and contain free quercetin, kaempferide and isorhamnetin.

More preferably, the content of total flavonol glycosides is calculated according to formula (1): content of total flavonol glycosides=(quercetin content+kaempferide content+isorhamnetin content)×2.51.

Preferably, the chromatographic peak area ratio of quercetin to kaempferide ($C_{16}H_{12}O_6$, CAS number 491-54-3) in the ginkgo biloba ketone ester capsule is 0.8-1.2, and the chromatographic peak area ratio of isorhamnetin ($C_{16}H_{12}O_7$, CAS number 207-545-5480-19-3) to quercetin is more than 0.15.

The three aglycones (quercetin, kaempferide and isorhamnetin) generated after the hydrolysis of ginkgo flavonoids in the ginkgo biloba ketone ester capsule have a certain proportional relationship, which to some extent may reflect and determine whether the raw materials and production processes are normalized or not, and may also be used to control product quality. The chromatographic peak area ratios of quercetin to kaempferol and isorhamnetin to quercetin are calculated according to the traditional methods for determining total flavonoid glycosides.

Preferably, the fingerprint spectrum of the ginkgo biloba ketone ester capsule includes four common fingerprint peaks as shown in the drawing: peak 1 is the fingerprint peak of rutin, peak 6 is the fingerprint peak of quercetin, peak 7 is the fingerprint peak of kaempferide, and peak 8 is the fingerprint peak of isorhamnetin.

Preferably, the similarity between the fingerprint spectrum of the ginkgo biloba ketone ester capsule and the chromatogram of the test product is greater than or equal to 0.90. The similarity between the fingerprint spectra of test products and ginkgo biloba ketone ester capsule is calculated and compared according to "Similarity Evaluation System for Chromatographic Fingerprint of Traditional Chinese Medicine" (version 2.0).

The contents of rutin, quercetin, bilobalide, ginkgolide J, total flavonol glycoside and terpene lactone, and the fingerprint spectrum of ginkgo biloba ketone ester capsule in the above ginkgo biloba ketone ester capsule are determined by high performance liquid chromatography (HPLC) in General Rules 0512 in Chinese Pharmacopoeia (2015 Edition) Volume IV. The contents of diflavonoid, total ginkgolic acids, ginkgolide M and Genistin are determined according to high performance liquid chromatography-mass spectrometry (HPLC-MS).

The above % are all mass percentages.

The second aspect of the present disclosure provides a method for preparing ginkgo biloba ketone ester capsules. The desired ginkgo biloba ketone ester capsules are obtained by mixing well the ginkgo biloba ketone ester raw material, dextrin, starch, low-substituted hydroxypropyl cellulose and carboxymethyl starch sodium according to the composition ratio, granulating, drying, then adding magnesium stearate, mixing well, and filling into the capsules.

Preferably, the method for preparing the ginkgo biloba ketone ester capsules includes the following operations:

A) according to the composition ratio, dividing the starch into a first part of starch and a second part of starch; preparing the second part of starch into a starch slurry, and then premixing the ginkgo biloba ketone ester raw material, dextrin, the first part of starch, low-substituted hydroxypropyl cellulose and carboxymethyl starch sodium; granulating and drying after spraying the starch slurry;

B) sieving and straightening the granules obtained by the granulating and drying, adding magnesium stearate for mixing;

C) filling capsules with the granules obtained by mixing, to obtain the desired ginkgo biloba ketone ester capsules.

Preferably, in operation A), the starch is corn starch.

Preferably, in operation A), the starch slurry is corn starch slurry. The starch slurry is used as a binding agent for granulation.

More preferably, the corn starch slurry is prepared by adding water to the second part of starch, stirring evenly and sieving.

Further preferably, the corn starch slurry is prepared by stirring the second part of starch with normal temperature water, then adding boiling water, stirring evenly and sieving.

Most preferably, the normal temperature water and the boiling water are both purified water.

Further preferably, the mass ratio of the second part of starch to the added water is 6:230-250. More preferably, the mass ratio of the second part of starch to the added water is 6:240.

Further preferably, the mesh number of the sieving is 70-90 mesh. Most preferably, the mesh number of the sieving is 80 mesh.

Preferably, in operation A), the amount of the second part of starch in the starch is small. As long as the amount of starch can be made into starch slurry, there is no strict dosage range for the second part of starch.

More preferably, the amount of the second part of starch does not exceed 10 wt % of the amount of the starch.

Preferably, in operation A), the pre-mixing, granulating and drying are carried out in a boiling dryer. The boiling dryer may be a conventional boiling dryer and can be purchased from the market.

More preferably, the outlet air temperature of the boiling dryer is 35-45° C., and the inlet air temperature is 80-105° C.

Further preferably, the outlet air temperature of the boiling dryer is 35° C., and the inlet air temperature is 95° C.

Preferably, in operation A), the time of the premixing is 10-12 minutes.

Preferably, in operation A), the material temperature when spraying the starch slurry is 54-56° C. More preferably, the material temperature when spraying the starch slurry is 55° C.

Preferably, in operation A), the spray pressure when spraying the starch slurry is 0.25-0.35 MPa.

Preferably, in operation A), the spray revolving speed when spraying the starch slurry is 40-60 revolutions per minute.

Preferably, in operation A), the oscillation time of the granulation is 110-130 seconds, and the oscillation frequency is 5-8 times. More preferably, the oscillation time of the granulation is 120 seconds, and the oscillation frequency is 6-7 times.

Preferably, in operation A), the stop-drying-material temperature is 60-64° C. More preferably, the stop-drying-material temperature is 62° C. The stop-drying-material temperature refers to stopping drying when a set temperature of the material is reached during drying.

Preferably, in operation A), the time for the drying is 15-30 minutes.

Preferably, in operation B), the mesh number of the sieving and straightening is 14-18 mesh. More preferably, the mesh number of the sieving and straightening is 16 mesh.

Preferably, in operation B), the mixing is performed in a mixer. The mixer may be a conventional mixer and can be purchased from the market.

More preferably, the mixer may be a multi-direction movement mixer.

Preferably, in operation B), the revolving speed of the mixing is 20-25 revolutions per minute.

Preferably, in operation B), the time for the mixing is 5-6 minutes.

Preferably, in operation C), the capsule is a gelatin empty capsule.

Preferably, in operation C), the size of the capsule is a No. 2 capsule with blue head and white body, and the capsule weight is 0.0612 g/capsule.

Preferably, in operation C), the filling of the capsules is performed on a capsule filling machine. The capsule filling machine may be a conventional capsule filling machine and can be purchased from the market.

Preferably, in operation C), after the capsules are filled, light inspection and polishing are also performed.

More preferably, the light inspection requires that the filled capsules are free of Torx head, crepe skin, notch, deflated head, bubble and empty granule, and have no adhesion, deformation and fracture.

More preferably, the polishing is performed on a polishing machine. The polishing machine may be a conventional polishing machine and can be purchased from the market.

Preferably, the composition ratio of the ginkgo biloba ketone ester capsules, in parts by weight, includes the following:
  35-45 parts of ginkgo biloba ketone ester raw materials;
  35-45 parts of dextrin;
  80-100 parts of starch;
  15-25 parts of low-substituted hydroxypropyl cellulose;
  6-10 parts of carboxymethyl starch sodium; and
  1-3 parts of magnesium stearate.

More preferably, the composition ratio of the ginkgo biloba ketone ester capsules, in parts by weight, includes the following:
  40 parts of ginkgo biloba ketone ester raw materials;
  40 parts of dextrin;
  90 parts of starch;
  20 parts of low-substituted hydroxypropyl cellulose;
  8 parts of carboxymethyl starch sodium; and
  2 parts of magnesium stearate.

More preferably, the CAS number of the low-substituted hydroxypropyl cellulose is 9004-65-3 or 78214-41-2.

More preferably, the ginkgo biloba ketone ester raw materials are ginkgo biloba leaves.

Further preferably, the ginkgo biloba leaves are dried ginkgo biloba nursery leaves. The ginkgo biloba nursery leaves are leaves of non-adult ginkgo trees, which are planted for the purpose of collecting ginkgo biloba leaves.

More further preferably, the drying conditions are: the drying temperature is 140-160° C., and the drying time is 6-15 minutes.

More further preferably, the ginkgo biloba nursery leaves meet the following requirements:

a) the content of total flavonol glycosides is greater than or equal to 0.85%;
b) the content of terpene lactones is greater than or equal to 0.40%;
c) the content of total ash is less than or equal to 10.0%;
d) the content of acid-insoluble ash is less than or equal to 2.0%;
e) the content of extractum is greater than or equal to 25.0%;
f) the chromatographic peak area ratio of quercetin to kaempferide is 0.65-1.2, and the chromatographic peak area ratio of isorhamnetin to quercetin is more than 0.15;
g) the content of impurity is less than or equal to 2.0%;
h) the content of water is less than or equal to 12.0%;
i) the content of sulfur dioxide residue is less than or equal to 150 mg/kg.

The definitions of the total flavonol glycosides and terpene lactones in the ginkgo biloba nursery leaves are the same as those of ginkgo biloba ketone ester capsules mentioned above. The definition of the chromatographic peak area ratio of flavonoid aglycones in the ginkgo biloba nursery leaves (that is, the chromatographic peak area ratio among quercetin, kaempferide and isorhamnetin) is the same as that of the above-mentioned ginkgo biloba ketone ester capsules.

The contents of total ash and acid-insoluble ash in the ginkgo biloba nursery leaves are determined according to the ash determination method described in General Rules 2302 in Chinese Pharmacopoeia (2015 Edition) Volume IV. The content of extractum in the ginkgo biloba nursery leaves is determined according to the extractum determination method described in General Rules 2201 in Chinese Pharmacopoeia (2015 Edition) Volume IV. The content of impurity in the ginkgo biloba nursery leaves is determined according to the impurity determination method described in General Rules 2301 in Chinese Pharmacopoeia (2015 Edition) Volume IV. The content of water in the ginkgo biloba nursery leaves is determined according to the water determination method described in General Rules 0832 in Chinese Pharmacopoeia (2015 Edition) Volume IV. The content of sulfur dioxide residue in the ginkgo biloba nursery leaves is determined according to the sulfur dioxide residue determination method described in General Rules 2331 in Chinese Pharmacopoeia (2015 Edition) Volume IV.

Preferably, the preparation method of the ginkgo biloba ketone ester raw material includes the following operations:
  1) adding ethanol aqueous solution to crushed ginkgo biloba leaves, heating at reflux for extraction, and then obtaining the filtrate by filtration;
  2) concentrating the filtrate and performing water-sedimentation, centrifuging the supernatant to obtain a centrifugal liquid;
  3) loading the centrifugal liquid onto a macroporous resin column, then washing with water and eluting with solvent to obtain a first eluent; the first eluent includes a low-concentration-solvent first eluent and a high-concentration-solvent first eluent;
  4) loading the low-concentration-solvent first eluent onto a polyamide column, then washing with water and eluting with ethanol to obtain a second eluent;
  5) combining and concentrating the second eluent with the high-concentration-solvent first eluent, and then extracting, drying, crushing, sieving, and mixing to obtain a desired ginkgo biloba ketone ester raw material.

More preferably, in operation 1), the crushed ginkgo biloba leaves are obtained by crushing ginkgo biloba leaves.

More preferably, in operation 1), the obtaining of the filtrate includes the following:
A) adding 60% ethanol aqueous solution to crushed ginkgo biloba leaves, heating at reflux for extraction, and then obtaining a first filtrate by filtration;
B) adding water to the residual medicine residue after the filtration in operation A), heating at reflux for extraction, and then obtaining a second filtrate by filtration;
C) combining and concentrating the second filtrate into a thick paste in operation B) and the first filtrate in operation A), dissolving, standing to cool, and filtering to obtain the desired filtrate.

More preferably, in operation A), the conditions of the heating at reflux for extraction are: 2 times of extraction; 3 hours for each extraction time.

More preferably, in operation B), the conditions of the heating at reflux for extraction are: 1 time of extraction; 0.5 hours for each extraction time.

More preferably, in operation B), the water is purified water.

More preferably, in operation C), the combining and concentrating is selected from one of a method of concentrating after combining or a method of combining after concentrating. The method of concentrating after combining is to combine the second filtrate with the first filtrate and then concentrate. The method of combining after concentrating is to concentrate the first filtrate first, and then combine with the second filtrate and continue to concentrate.

More preferably, in operation C), the dissolving is the dissolving by using hot water. The hot water is purified water which has been heated to 60-100° C.

Preferably, in operation 2), the filtrate is concentrated to have no alcohol smell.

Preferably, in operation 2), the relative density of the concentrated filtrate is 1.04-1.08.

Preferably, in operation 2), the purified water added in the water-sedimentation is 1.5-2.5 times the amount of the ginkgo biloba powder. Specifically, that the purified water added is 1.5-2.5 times the amount of the ginkgo biloba powder means that 1.5-2.5 ml of purified water is added to each 1 g of the ginkgo biloba powder.

Preferably, in operation 2), the water-sedimentation is the interlayer cooling in 5-7° C. cooling water for 12-24 hours.

Preferably, in operation 2), the centrifugation conditions are as follows: the centrifugal speed is 13,000-15,000 rpm, and the centrifugal time per 3-5 L of supernatant is 0.75-1.25 min.

More preferably, the centrifugation conditions are as follows: the centrifugal speed is 14,000 rpm, and the centrifugal time per 3-5 L of supernatant is 1.00 min.

In operation 2), the above-mentioned concentration, water-sedimentation and centrifugation can ensure the optimization of the quality conditions of the ginkgo biloba ketone ester raw material of the present disclosure, so that the quality of the ginkgo biloba ketone ester capsule is better.

Preferably, in operation 3), the washing with water is forward-washing with purified water for 1-2 hours first, and then backwashing for 0.5-1.5 hours. The washing with water can ensure the optimization of quality conditions such as ginkgolic acids and ignition residue in the ginkgo biloba ketone ester raw material of the present disclosure, so that the quality of the ginkgo biloba ketone ester capsule is better.

More preferably, the washing with water is forward-washing with purified water for 1.5 hours first, and then backwashing for 1 hour.

Preferably, in operation 3), the eluting with solvent is eluting with 18% ethanol aqueous solution, 30% ethanol aqueous solution and 50% ethanol aqueous solution in sequence to obtain 18% ethanol eluent, 30% ethanol eluent and 50% ethanol eluent, respectively.

Preferably, in operation 3), the high-concentration-solvent first eluent is a 50% ethanol eluent.

Preferably, in operation 3), the low-concentration-solvent first eluent is a combined solution of an 18% ethanol eluent and a 30% ethanol eluent.

Preferably, in operation 4), the washing with water is forward-washing by using purified water 0.5-2 times the volume of the polyamide column. More preferably, the washing with water is forward-washing by using purified water 1 time the volume of the polyamide column. The washing with water is capable of further removing impurities, including ginkgolic acids, from the ginkgo biloba ketone ester.

Preferably, in operation 4), the low-concentration-solvent first eluent is concentrated to have no alcohol smell before being loaded onto the polyamide column.

Preferably, in operation 4), the second eluent is an ethanol eluent.

Preferably, in operation 5), the combining and concentrating is selected from one of a method of concentrating after combining or a method of combining after concentrating. The method of concentrating after combining is to combine the second eluent with the high-concentration-solvent first eluent and then concentrate. The method of combining after concentrating is to concentrate the high-concentration-solvent first eluent first, and then combine with the second eluent and continue to concentrate.

Preferably, in operation 5), the second eluent and the high-concentration-solvent first eluent are concentrated to have no alcohol smell.

Preferably, in operation 5), the extracting is carried out using cyclohexane as a solvent. After the extracting, the cyclohexane extract is discarded.

Preferably, in operation 5), the drying is selected from spray drying or vacuum drying.

More preferably, before the vacuum drying, the concentrated solution needs to be concentrated into a thick paste.

Preferably, in operation 5), the sieving is by passing through an 80-100 mesh sieve. More preferably, the sieving is by passing through a 90-100 mesh sieve. Most preferably, the sieving is by passing through a 100 mesh sieve. The sieving can ensure that the particle size of the ginkgo biloba ketone ester raw material of the present disclosure is finer, so that the quality of the ginkgo biloba ketone ester capsule is better.

Preferably, in operation 5), the conditions for the mixing are: the mixing equipment is a total mixer; the mixing speed is 10-12 rpm; the mixing time is 1.5-2.5 hours. The mixing can ensure better uniformity of the ginkgo biloba ketone ester raw material of the present disclosure, so that the quality of the ginkgo biloba ketone ester capsule is better.

More preferably, the conditions for the mixing are: the mixing equipment is a total mixer; the mixing speed is 11 rpm; the mixing time is 2 hours.

The third aspect of the present disclosure provides the use of the method for preparing ginkgo biloba ketone ester capsule in the preparation of ginkgo biloba ketone ester capsule.

As mentioned above, the present disclosure provides a ginkgo biloba ketone ester capsule and a preparation method thereof. Through optimized preparation operations and conditions, a high-quality ginkgo biloba ketone ester capsule can be obtained. Compared with the ginkgo biloba ketone ester capsule prepared by traditional methods, the ginkgo biloba ketone ester capsule of the present disclosure has stable quality and a low unqualified rate. The consistency of different batches of ginkgo biloba ketone ester capsules is good. In particular, the ginkgo biloba ketone ester capsule can effectively control ginkgolic acids, preventing the use of high-ginkgolic-acid raw materials in the ginkgo biloba ketone ester capsules, so as to effectively improve the safety of ginkgo biloba ketone ester capsules.

BRIEF DESCRIPTION OF THE DRAWINGS

The drawing shows the fingerprint spectrum of the ginkgo biloba ketone ester capsule according to the present disclosure; in the fingerprint spectrum, 1: rutin; 6: quercetin; 7: kaempferide; 8: isorhamnetin.

DETAILED DESCRIPTION OF THE PREFERRED EMBODIMENTS

The present disclosure is further described below with reference to specific embodiments. It should be understood that the embodiments are just for describing the present disclosure instead of limiting the scope of the present disclosure.

The embodiments of the present disclosure will be described below. Those skilled in the art can easily understand other advantages and effects of the present disclosure according to contents disclosed by the specification. The present disclosure can also be implemented or applied through other different exemplary embodiments. Various modifications or changes can also be made to all details in the specification based on different points of view and applications without departing from the spirit of the present disclosure.

It should be noted that processing equipment or devices not specifically noted in the following embodiments are all conventional equipment or devices in the field. All pressure values and ranges refer to relative pressures. The reagents used below are all conventional reagents in the field. The instruments used below are all conventional instruments in the field.

In addition, it should be understood that one or more method steps mentioned in the present disclosure are not exclusive of other method steps that may exist before or after the combined steps or that other method steps may be inserted between these explicitly mentioned steps, unless otherwise stated; it should also be understood that the combined connection relationship between one or more equipment/devices mentioned in the present disclosure does not exclude that there may be other equipment/devices before or after the combined equipment/devices or that other equipment/devices may be inserted between these explicitly mentioned equipment/devices, unless otherwise stated. Moreover, unless otherwise stated, the numbering of each method step is only a convenient tool for identifying each method step, and is not intended to limit the order of each method step or to limit the scope of the present disclosure. The change or adjustment of the relative relationship shall also be regarded as the scope in which the present disclosure may be implemented without substantially changing the technical content.

Embodiment 1

Dried ginkgo biloba nursery leaves are crushed to obtain crushed ginkgo biloba leaves. Adding 60% ethanol aqueous solution to the crushed ginkgo biloba leaves, extracting twice by heating at reflux, each for 3 hours, and obtaining a first filtrate by filtration. Then, adding water to the filtered medicine residue left after the filtration, extracting for one time by heating at reflux with the extraction time of 0.5 hours, and then obtaining a second filtrate by filtration. Combining and concentrating the second filtrate and the first filtrate into a thick paste. The combining and concentrating may be conducted by concentrating after combining or combining after concentrating. Dissolving by purified water which has been heated to 60-100° C., standing to cool, and filtering to obtain a filtrate. Concentrating the filtrate to a relative density of 1.04-1.08 and without alcohol smell, adding purified water that is 1.5-2.5 times the amount of the ginkgo biloba leaf powder, cooling in interlayer in 5-7° C. cooling water for 12-24 h, and centrifuging the supernatant at a speed of 14,000 rpm to obtain a centrifugal liquid. Loading the centrifugal liquid onto a macroporous resin column, forward-washing with purified water for 1.5 hours first, and then backwashing for 1 hour. Eluting with 18% ethanol aqueous solution, 30% ethanol aqueous solution and 50% ethanol aqueous solution in sequence to obtain 18% ethanol eluent, 30% ethanol eluent and 50% ethanol eluent, respectively, which are the first eluents. In the first eluents, the 50% ethanol eluent is the high-concentration-solvent first eluent, and the combined solution of the 18% ethanol eluent and the 30% ethanol eluent is the low-concentration-solvent first eluent. The low-concentration-solvent first eluent is then concentrated to have no alcohol smell. Loading the low-concentration-solvent first eluent onto a polyamide column, forward-washing with purified water that is 1 times the volume of the polyamide column, and then eluting with ethanol to obtain an ethanol eluent, which is the second eluent. Combining and concentrating the second eluent and the high-concentration-solvent first eluent until there is no alcohol smell. The combining and concentrating may be conducted by concentrating after combining or combining after concentrating. After the concentrate is extracted with cyclohexane, the cyclohexane extract is discarded. Then, spray-drying the concentrated solution, or concentrating the concentrated solution into a thick paste and vacuum-drying the thick paste. Pulverizing the dried products, passing through a 100-mesh sieve, and mixing in a total mixer at a speed of 11 rpm for 2 hours to obtain the desired ginkgo biloba ketone ester raw material Sample 1#.

Control Example 1

Conventional ginkgo biloba leaves are crushed to obtain crushed ginkgo biloba leaves. Adding 60% ethanol aqueous solution to the crushed ginkgo biloba leaves, extracting twice by heating at reflux, each for 3 hours, and obtaining a first filtrate by filtration. Then, adding water to the filtered medicine residue left after the filtration, extracting for one time by heating at reflux with the extraction time of 0.5 hours, and then obtaining a second filtrate by filtration. Combining and concentrating the second filtrate into a thick paste and the first filtrate. The combining and concentrating may be conducted by concentrating after combining or combining after concentrating. Dissolving by purified water which has been heated to 60-100° C., standing to cool, and filtering to obtain a filtrate. Loading the filtrate onto a macroporous resin column, eluting with 18% ethanol aqueous solution, 30% ethanol aqueous solution and 50% ethanol aqueous solution in sequence to obtain 18% ethanol eluent, 30% ethanol eluent and 50% ethanol eluent, respectively, which are the first eluents. In the first eluents, the 50% ethanol eluent is the high-concentration-solvent first eluent, and the combined solution of the 18% ethanol eluent and the 30% ethanol eluent is the low-concentration-solvent first eluent. The low-concentration-solvent first eluent is then concentrated to have no alcohol smell. Loading the low-concentration-solvent first eluent onto a polyamide column, eluting with ethanol to obtain an ethanol eluent, which is the second eluent. Combining and concentrating the second eluent and the high-concentration-solvent first eluent until there is no alcohol smell. The combining and concentrating may be conducted by concentrating after combining or combining after concentrating. After the concentrate is extracted with cyclohexane, the cyclohexane extract is discarded. Then, spray-drying the concentrated solution, or concentrating the concentrated solution into a thick paste and vacuum-drying the thick paste. Pulverizing the dried products to obtain the desired ginkgo biloba ketone ester raw material Control Sample 1*.

Control Example 2

Conventional ginkgo biloba leaves, ginkgo biloba root bark and Fructus Sophorae are crushed to obtain crushed ginkgo biloba. Adding 60% ethanol aqueous solution to the crushed ginkgo biloba, extracting twice by heating at reflux, each for 3 hours, and obtaining a first filtrate by filtration. Then, adding water to the filtered medicine residue left after the filtration, extracting for one time by heating at reflux with the extraction time of 0.5 hours, and then obtaining a second filtrate by filtration. Combining and concentrating the second filtrate and the first filtrate into a thick paste. The combining and concentrating may be conducted by concentrating after combining or combining after concentrating. Dissolving by purified water which has been heated to 60-100° C., standing to cool, and filtering to obtain a filtrate. Loading the filtrate onto a macroporous resin column, eluting with 18% ethanol aqueous solution, 30% ethanol aqueous solution and 50% ethanol aqueous solution in sequence to obtain 18% ethanol eluent, 30% ethanol eluent and 50% ethanol eluent, respectively, which are the first eluents. In the first eluents, the 50% ethanol eluent is the high-concentration-solvent first eluent, and the combined solution of the 18% ethanol eluent and the 30% ethanol eluent is the low-concentration-solvent first eluent. The low-concentration-solvent first eluent is then concentrated to have no alcohol smell. Loading the low-concentration-solvent first eluent onto a polyamide column, eluting with ethanol to obtain an ethanol eluent, which is the second eluent. Combining and concentrating the second eluent and the high-concentration-solvent first eluent until there is no alcohol smell. The combining and concentrating may be conducted by concentrating after combining or combining after concentrating. After the concentrate is extracted with cyclohexane, the cyclohexane extract is discarded. Then, spray-drying the concentrated solution, or concentrating the concentrated solution into a thick paste and vacuum-drying the thick paste. Pulverizing the dried products to obtain the desired ginkgo biloba ketone ester raw material Control Sample 2*.

Embodiment 2

Taking 26.40 kg of corn starch, and dividing the corn starch into a first part of starch and a second part of starch. Taking 0.60 kg of corn starch as the second part of starch, adding an appropriate amount of purified water, stirring evenly and placing in a slurry-mixing container, then adding boiling purified water to 24.00 kg, stirring evenly, and passing through an 80-mesh sieve to prepare the starch slurry. Then taking 12.60 kg of ginkgo biloba ketone ester raw material Sample 1#, 12.00 kg of dextrin, 25.80 kg of the first part of starch, 6.00 kg of low-substituted hydroxypropyl cellulose and 2.40 kg of carboxymethyl starch sodium, putting all the above materials into a boiling dryer. Starting the boiling dryer, setting the outlet air temperature of the boiling dryer as 35° C., and the inlet air temperature as 95° C. Premixing for 10-12 minutes. When the temperature of the materials is heated to 55° C., turning on the spray system to control the spray pressure to be 0.25-0.35 MPa and the spray revolving speed to be 40-60 rpm, and spraying the starch slurry. Granulating and drying simultaneously under the conditions that the oscillation time is 120 seconds and the oscillation frequency is 6-7 times, setting the material temperature as 62° C. after the granulation is completed, stopping drying when the set material temperature is reached. The whole drying time is 15-30 minutes.

The granules obtained by granulating and drying are straightened after being sieved through a 16 mesh shaking sieve, then put into a multi-direction movement mixer with a rotating speed of 20-25 r/min. Adding 0.60 kg of magnesium stearate, and mixing for 5-6 minutes. Filling the granules obtained by the mixing with blue-headed and white-body No. 2 capsules, and the filling speed is 80-110 (potentiometer). By light inspection, the filled capsules shall be free of Torx head, crepe skin, notch, deflated head, bubble or empty granule, and have no adhesion, deformation or fracture. Polishing the capsules after the light inspection. The required ginkgo biloba ketone ester capsule Sample 1# is obtained. Each capsule of ginkgo biloba ketone ester capsule Sample 1# has a loading weight of 0.2 g. The above-mentioned feeding amounts comply with the quality standard $WS_3$-227(Z-028)-2002(Z) and the regulations of Chinese Pharmacopoeia (2015 Edition) Volume IV, and fall within the composition ratio of ginkgo biloba ketone ester capsule.

Embodiment 3

Taking 90 kg of corn starch, and dividing the corn starch into a first part of starch and a second part of starch. Taking 1.80 kg of corn starch as the second part of starch, adding an appropriate amount of purified water, stirring evenly and placing in a slurry-mixing container, then adding boiling purified water to 72.00 kg, stirring evenly, and passing through an 80-mesh sieve to prepare the starch slurry. Then taking 40 kg of ginkgo biloba ketone ester raw material Sample 1#, 40 kg of dextrin, 88.20 kg of the first part of starch, 20 kg of low-substituted hydroxypropyl cellulose and 8 kg of carboxymethyl starch sodium, putting all the above materials into a boiling dryer. Starting the boiling dryer, setting the outlet air temperature of the boiling dryer as 35° C., and the inlet air temperature as 95° C. Premixing for 11 minutes. When the temperature of the materials is heated to 55° C., turning on the spray system to control the spray pressure to be 0.30 MPa and the spray revolving speed to be 50 rpm, and spraying the starch slurry. Granulating and drying simultaneously under the conditions that the oscillation time is 120 seconds and the oscillation frequency is 6-7 times, setting the material temperature as 62° C. after the granulation is completed, stopping drying when the set material temperature is reached. The whole drying time is 25 minutes.

The granules obtained by granulating and drying are straightened after being sieved through a 16 mesh shaking sieve, then put into a multi-direction movement mixer with a rotating speed of 20-25 r/min. Adding 2 kg of magnesium stearate, and mixing for 5-6 minutes. Filling the granules obtained by the mixing with blue-headed and white-body No. 2 capsules, and the filling speed is 80-110 (potentiometer). By light inspection, the filled capsules shall be free of Torx head, crepe skin, notch, deflated head, bubble or empty granule, and have no adhesion, deformation or fracture. Polishing the capsules after the light inspection. The required ginkgo biloba ketone ester capsule Sample 2# is obtained. Each capsule of ginkgo biloba ketone ester capsule Sample 2# has a loading weight of 0.2 g. The above-mentioned feeding amounts comply with the quality standard $WS_3$-227(Z-028)-2002(Z) and the regulations of Chinese Pharmacopoeia (2015 Edition) Volume IV, and fall within the composition ratio of ginkgo biloba ketone ester capsule.

Control Example 3

Taking 12.60 kg of ginkgo biloba ketone ester raw material Control Sample 1*, 12.00 kg of dextrin, 26.40 kg of starch, 6.00 kg of low-substituted hydroxypropyl cellulose and 2.40 kg of carboxymethyl starch sodium. According to the conventional method for preparing ginkgo biloba ketone ester capsules, mixing well, granulating, drying, then adding 0.60 kg of magnesium stearate, mixing well, and filling into the capsules, to obtain the desired ginkgo biloba ketone ester capsule Control Sample 1*. The loading weight of each capsule of ginkgo biloba ketone ester capsule Control Sample 1* is 0.2 g. The above-mentioned feeding amounts comply with the quality standard $WS_3$-227(Z-028)-2002(Z) and the regulations of Chinese Pharmacopoeia (2015 Edition) Volume IV, and fall within the composition ratio of ginkgo biloba ketone ester capsule.

At the same time, taking 12.60 kg of ginkgo biloba ketone ester raw material Control Sample 2*, 12.00 kg of dextrin, 26.40 kg of starch, 6.00 kg of low-substituted hydroxypropyl cellulose and 2.40 kg of carboxymethyl starch sodium. According to the conventional method for preparing ginkgo biloba ketone ester capsules, mixing well, granulating, drying, then adding 0.60 kg of magnesium stearate, mixing well, and filling into the capsules, to obtain the desired ginkgo biloba ketone ester capsule Control Sample 2*. The loading weight of each capsule of ginkgo biloba ketone ester capsule Control Sample 2* is 0.2 g. The above-mentioned feeding amounts comply with the quality standard $WS_3$-227 (Z-028)-2002(Z) and the regulations of Chinese Pharmacopoeia (2015 Edition) Volume IV, and fall within the composition ratio of ginkgo biloba ketone ester capsule.

Embodiment 4

Taking 20 capsules of contents from the ginkgo biloba ketone ester capsule Sample 1# (prepared in Embodiment 2), the ginkgo biloba ketone ester capsule Control Samples 1* and 2* (prepared in Control Example 3), respectively mixing well, precisely weighing, grinding fine, and taking 0.5 g of the powder. Precisely weighing the powder, placing the powder in a conical flask with stopper, precisely adding 10 ml of a mixed solution of 70% methanol-70% ethanol (1:1), and extracting by shaking (frequency: 500 times per minute) for 30 minutes. Taking out the solution for centrifugation to obtain the supernatant (or, filtering the solution to obtain the subsequent filtrates), to obtain the test product solutions A1, A2 and A3.

At the same time, taking appropriate amounts of rutin reference substance and quercetin reference substance, precisely weighing the reference substances. The reference substances are added with methanol to prepare a mixed solution containing 250 µg of rutin and 25 µg of quercetin per 1 ml, to obtain the reference solution.

Precisely pipetting 10 µl from the test product solutions A1, A2, A3 and the reference solution, respectively, which are then determined by high performance liquid chromatography (HPLC) in General Rules 0512 in Chinese Pharmacopoeia (2015 Edition) Volume IV. The conditions of the high-performance liquid chromatography are as follows: octadecylsilane chemically bonded silica gel serves as a filler; acetonitrile serves as mobile phase A, and 0.4% phosphoric acid solution serves as mobile phase B. Gradient elution is performed according to the specification in Table 1 below; the detection wavelength is 400 nm. The number of theoretical plates calculated by the rutin peak is no less than 8000.

TABLE 1

| Time (minutes) | Mobile phase A (%) | Mobile phase B (%) |
| --- | --- | --- |
| 0~35 | 15 | 85 |
| 35~80 | 20 | 80 |

The determination result shows that in ginkgo biloba ketone ester capsule Sample 1#, the content of rutin is 1.08 mg/capsule, and the value is ≤1.28 mg/capsule; the content of quercetin is 0.112 mg/capsule, and the value is ≤0.152 mg/capsule. In ginkgo biloba ketone ester capsule Control Sample 1*, the content of rutin is 1.38 mg/capsule, and the value is ≤1.60 mg/capsule; the content of quercetin is 0.158 mg/capsule, and the value is ≤0.160 mg/capsule. In ginkgo biloba ketone ester capsule Control Sample 2*, the content of rutin is 1.93 mg/capsule, and the value is >1.60 mg/capsule; the content of quercetin is 0.198 mg/capsule, and the value is >0.160 mg/capsule. It can be seen from the above content values that the contents of rutin and quercetin in ginkgo biloba ketone ester capsule Sample 1# and ginkgo biloba ketone ester capsule Control Sample 1* are within the specified value range, indicating that there is no adulterated foreign substances, which means, the production process is normal, and the product quality is good. The contents of rutin and quercetin in ginkgo biloba ketone ester capsule Sample 1# are both lower than those of ginkgo biloba ketone ester capsule Control Sample 1*, indicating that the product quality of ginkgo biloba ketone ester capsule Sample 1# is better than that of ginkgo biloba ketone ester capsule Control Sample 1*. The contents of rutin and quercetin in ginkgo biloba ketone ester capsule Control Sample 2* exceed the specified value range, indicating that there may be adulterated foreign substances, and the product quality is poor.

Embodiment 5

Taking 20 capsules of contents from the ginkgo biloba ketone ester capsule Sample 1# (prepared in Embodiment 2), the ginkgo biloba ketone ester capsule Control Samples 1* and 2* (prepared in Control Example 3), respectively mixing well, precisely weighing, grinding fine, taking 1 g of powder, and spray-drying the powder. Drying the samples in a vacuum oven at a temperature of <80° for 2 hours; or concentrating a liquid extract to a relative density of 1.2, and then drying with an inlet air temperature of 160-165° and an outlet air temperature of 95-100°.

The determination result shows that in ginkgo biloba ketone ester capsule Sample 1#, the content of ethanol residue is 0.06 mg/capsule, and the value is ≤0.08 mg/capsule. In ginkgo biloba ketone ester capsule Control Sample 1*, the content of ethanol residue is 0.13 mg/capsule, and the value is ≤0.2 mg/capsule. In ginkgo biloba ketone ester capsule Control Sample 2*, the content of ethanol residue is 0.17 mg/capsule, and the value is ≤0.2 mg/capsule. It can be seen from the above contents that the ethanol residues in ginkgo biloba ketone ester capsule Sample 1#, ginkgo biloba ketone ester capsule Control Sample 1* and 2* all meet the control requirements. However, ginkgo biloba ketone ester capsule Sample 1# has the least residual ethanol and the best quality. Ginkgo biloba ketone ester capsule Control Sample 1* and 2* have almost the same amount of residual ethanol, but the amount of residual ethanol of Control Sample 1* and 2* is higher than that of ginkgo biloba ketone ester capsule Sample 1#, therefore has inferior quality.

Embodiment 6

Taking 20 capsules of contents from the ginkgo biloba ketone ester capsule Sample 1# (prepared in Embodiment 2), the ginkgo biloba ketone ester capsule Control Samples 1* and 2* (prepared in Control Example 3), respectively mixing well, precisely weighing, grinding fine, and taking 0.6 g of powder. Precisely weighing the powder, placing the powder in a 50 ml centrifuge tube with a stopper, adding 15 ml of 30% ethanol, shaking well, adding 20 ml of diethyl ether, shaking well, standing for a while, carefully opening the lid, tightening the lid after deflation, vortexing (3000 times per minute) for 1 minute, centrifuging (4000 rpm) for 10 minutes, separating the supernatant. Adding diethyl ether to the residue, repeating the above operations 3 times, 15 ml of diethyl ether each time. Combining the four diethyl ether solutions, concentrating under reduced pressure to near dryness (do not evaporate to dryness), adding a proper amount of methanol and dissolving by ultrasonic, and completely transferring to a 5 ml measuring flask. Centrifuging to obtain the supernatant (or passing through a 0.45 μm filter membrane to obtain the subsequent filtrates), to obtain the test product solutions B1, B2 and B3.

At the same time, taking appropriate amounts of bilobalide reference substance, ginkgolide A reference substance, ginkgolide B reference substance, ginkgolide C reference substance and ginkgolide J reference substance, and precisely weighing the reference substances. The reference substances are added with methanol to prepare mixed solutions each containing 1.0 mg, 0.3 mg, 0.7 mg and 0.4 mg of each reference substance per 1 ml, which is the reference solution.

Precisely pipetting 5 μl and 10 μl from the reference solution, and 10 μl from the test product solutions B1, B2 and B3, respectively, which are then determined by high performance liquid chromatography (HPLC) in General Rules 0512 in Chinese Pharmacopoeia (2015 Edition) Volume IV. The contents of bilobalide, ginkgolide A, ginkgolide B, ginkgolide C and ginkgolide J are calculated by using an external standard two-point logarithmic equation. The conditions of the high-performance liquid chromatography are as follows: octadecylsilane chemically bonded silica gel serves as a filler; methanol serves as mobile phase A, and water serves as mobile phase B. Gradient elution is performed according to the specification in Table 2 below; the detection is performed by an evaporative light scattering detector. The number of theoretical plates calculated by the bilobalide peak is no less than 10000.

TABLE 2

| Time (minutes) | Mobile phase A (%) | Mobile phase B (%) |
|---|---|---|
| 0~15 | 30 | 70 |
| 15~30 | 40 | 60 |

The determination shows that the contents of terpene lactones in the ginkgo biloba ketone ester capsule Sample 1# and ginkgo biloba ketone ester capsule Control Sample 1* are calculated as dry products, and are calculated by the total contents of bilobalide, ginkgolide A, ginkgolide B and ginkgolide C. The contents of terpene lactones in the ginkgo biloba ketone ester capsule Sample 1# and ginkgo biloba ketone ester capsule Control Sample 1* are 3.9 mg/capsule and 2.8 mg/capsule, respectively, which are within the specified data range of 2.4-4.8 mg/capsule. However, the content of terpene lactones in the ginkgo biloba ketone ester capsule Control Sample 2* is calculated as dry products, and is calculated by the total contents of bilobalide, ginkgolide A, ginkgolide B and ginkgolide C. The content of terpene lactones in the ginkgo biloba ketone ester capsule Control Sample 2* is 1.7 mg/capsule, which is lower than the specified data range of 2.4-4.8 mg/capsule. Terpene lactones, as unique components in ginkgo biloba, are the main effective components of ginkgo biloba ketone ester capsules in blood-activating and stasis-eliminating as well as in the treatment of angina pectoris, coronary heart disease and cerebral arteriosclerosis. Therefore, terpene lactones in ginkgo biloba ketone ester capsules need to be within a specified data range. It can be seen that the ginkgo biloba ketone ester capsule Control Sample 2* has a poor treatment effect. Ginkgo biloba ketone ester capsule Sample 1# and ginkgo biloba ketone ester capsule Control Sample 1* both have good therapeutic effects. However, the content of terpene lactones in ginkgo biloba ketone ester capsule Sample 1# is even higher, which is within a specified capsule data range of 3.6-4.8 mg/capsule. Compared with ginkgo biloba ketone ester capsule Control Sample 1*, ginkgo biloba ketone ester capsule Sample 1# has better therapeutic effect.

At the same time, the determination shows that the contents of bilobalide in the ginkgo biloba ketone ester capsule Sample 1# and ginkgo biloba ketone ester capsule Control Sample 1* are 1.87 mg/capsule and 1.28 mg/capsule, respectively, which are within a specified data range of 1.04-2.08 mg/capsule. The content of bilobalide in ginkgo biloba ketone ester capsule Control Sample 2* is 0.88 mg/capsule, which is lower than the specified data range of 1.04-2.08 mg/capsule. Bilobalide in ginkgo biloba ketone ester capsules has an anti-PAF effect as well as nutritional functions for nerves. Therefore, the ginkgo biloba ketone ester capsule Control Sample 2* has a poor treatment effect. Ginkgo biloba ketone ester capsule Sample 1# and ginkgo biloba ketone ester capsule Control Sample 1* both have good therapeutic effects. However, the content of bilobalide in ginkgo biloba ketone ester capsule Sample 1# is more accurate, which is within a specified capsule data range of 1.44-1.92 mg/capsule. Compared with ginkgo biloba ketone ester capsule Control Sample 1*, ginkgo biloba ketone ester capsule Sample 1# has a better therapeutic effect.

In addition, the determination shows that the contents of ginkgolide J in the ginkgo biloba ketone ester capsule Sample 1# and ginkgo biloba ketone ester capsule Control Sample 1* are 0.16 mg/capsule and 0.10 mg/capsule, respectively, which are within a specified data range of 0.04-0.20 mg/capsule. The content of ginkgolide J in ginkgo biloba ketone ester capsule Control Sample 2* is 0.01 mg/capsule, which is lower than the specified data range of 0.04-0.20 mg/capsule. Ginkgolide J in ginkgo biloba ketone ester capsules also has anti-PAF effect. Therefore, the ginkgo biloba ketone ester capsule Control Sample 2* has a poor treatment effect. Ginkgo biloba ketone ester capsule Sample 1# and ginkgo biloba ketone ester capsule Control Sample 1* both have good therapeutic effects. However, the content of Ginkgolide J in ginkgo biloba ketone ester capsule Sample 1# is even higher, which is within a specified data range of 0.12-0.20 mg/capsule. Compared with ginkgo biloba ketone ester capsule Control Sample 1*, ginkgo biloba ketone ester capsule Sample 1# has a better therapeutic effect.

Embodiment 7

Taking 20 capsules of contents from the ginkgo biloba ketone ester capsule Sample 1# (prepared in Embodiment 2), the ginkgo biloba ketone ester capsule Control Samples 1* and 2* (prepared in Control Example 3), respectively mixing well, precisely weighing, grinding fine, and taking 0.1 g of powder. Precisely weighing the powder, extracting by ultrasonic with 5 mL ethanol for 10 min, centrifuging at 3000 rpm for 10 min, and then taking the supernatant. Repeating the above ultrasonic extraction for 3 times. Combining the supernatant and bringing to volume with a 25 mL volumetric flask, to obtain the test product solutions C1, C2 and C3.

At the same time, respectively taking appropriate amounts of Amentoflavone reference substance, Bilobetin reference substance and Ginkgetin reference substance, and precisely weighing the reference substances. The reference substances are added with ethanol to prepare a mixed solution with a certain concentration of Amentoflavone, Bilobetin and Ginkgetin, which is the reference solution.

Precisely pipetting 10 μl from the test product solutions C1, C2, C3 and the reference solution, respectively, then determining by high performance liquid chromatography-mass spectrometry (HPLC-MS) in General Rules 0512 and 0431 in Chinese Pharmacopoeia (2015 Edition) Volume IV. The conditions of the HPLC-MS are as follows: octadecylsilane chemically bonded silica gel serves as a filler; methanol-1% glacial acetic acid solution (90:10) serves as the mobile phase, eluting isocratically, fully cleaning with methanol-1% glacial acetic acid solution (99:1) that is at least 10 times the volume of the column after all the components to be determined have reached the peak; triple quadrupole mass spectrometer is used for multiple reaction monitoring (MRM) under electrospray ionization (ESI) negative ion mode.

The determination shows that the contents of biflavonoids in ginkgo biloba ketone ester capsule Sample 1# and ginkgo biloba ketone ester capsule Control Sample 1* are 0.003 mg/capsule and 0.005 mg/capsule, respectively. That is, the total contents of Amentoflavone, Bilobetin and Ginkgetin in ginkgo biloba ketone ester capsule Sample 1# and ginkgo biloba ketone ester capsule Control Sample 1* are all less than or equal to 0.008 mg/capsule. The content of biflavonoids in ginkgo biloba ketone ester capsule Control Sample 2* is 0.014 mg/capsule. That is, the total contents of Amentoflavone, Bilobetin and Ginkgetin in ginkgo biloba ketone ester capsule Control Sample 2* is higher than 0.008 mg/capsule. The content of biflavonoids must be controlled due to their allergenicity. The content of biflavones in ginkgo biloba ketone ester capsule Control Sample 2*exceeds the limit, which will make patients more susceptible to allergy. The contents of biflavonoids in ginkgo biloba ketone ester capsule Sample 1# and ginkgo biloba ketone ester capsule Control Sample 1* are within the limit. However, ginkgo biloba ketone ester capsule Sample 1# has a lower biflavonoids content, which can reach 0.004 mg/capsule or less, and is less likely to cause sensitization.

Embodiment 8

Taking 20 capsules of contents from the ginkgo biloba ketone ester capsule Sample 1# (prepared in Embodiment 2), the ginkgo biloba ketone ester capsule Control Samples 1* and 2* (prepared in Control Example 3), respectively mixing well, precisely weighing, grinding fine, and taking 0.1 g of powder. Precisely weighing the powder, extracting by ultrasonic with 5 mL of 50% methanol for 10 min, centrifuging at 3000 rpm for 10 min, and then taking the supernatant. Repeating the above ultrasonic extraction 3 times. Combining the supernatant and bringing to volume with a 25 mL volumetric flask, to obtain the test product solutions D1, D2 and D3.

At the same time, respectively taking appropriate amounts of Genistin reference substance and ginkgolide M reference substance, and precisely weighing the reference substances. The reference substances are added with methanol to prepare a mixed solution with a certain concentration of Genistin and ginkgolide M, which is the reference solution.

Precisely pipetting 10 μl from the test product solutions D1, D2, D3 and the reference solution, respectively, then determining by high performance liquid chromatography-mass spectrometry (HPLC-MS) in General Rules 0512 and 0431 in Chinese Pharmacopoeia (2015 Edition) Volume IV. The conditions of the HPLC-MS are as follows: octadecylsilane chemically bonded silica gel serves as a filler; methanol-1% glacial acetic acid solution (90:10) serves as the mobile phase, eluting isocratically, fully cleaning with methanol-1% glacial acetic acid solution (99:1) that is at least 10 times the volume of the column after all the components to be determined have reached the peak; triple quadrupole mass spectrometer is used for multiple reaction monitoring (MRM) under electrospray ionization (ESI) negative ion mode.

It can be known from the determination that neither the ginkgo biloba ketone ester capsule Sample 1# nor the ginkgo biloba ketone ester capsule Control Sample 1* contains Genistin and ginkgolide M. The ginkgo biloba ketone ester capsule Control Sample 2* contains Genistin and ginkgolide M. Genistin is a component present in Fructus Sophorae, ginkgolide M is a component present in ginkgo biloba root bark, neither of the above components is present in ginkgo biloba leaves. Therefore, the detection of the above components in the ginkgo biloba ketone ester capsule Control Sample 2* means that Fructus Sophorae and ginkgo biloba root bark are illegally added to the ginkgo biloba ketone ester capsule Control Sample 2*, indicating there are adulterated foreign substances. There are no adulterated foreign substances in ginkgo biloba ketone ester capsule Sample 1# and ginkgo biloba ketone ester capsule Control Sample 1*, indicating the product quality is good.

Embodiment 9

Taking 20 mg of the rutin reference substance, precisely weighing the rutin reference substance, placing the rutin reference substance in a 100 ml measuring flask, adding 70 ml of 70% ethanol, heating slightly in a water bath for dissolving, cooling, diluting to the mark with 70% ethanol, and shaking well to obtain the reference solution (containing 0.2 mg of anhydrous rutin per 1 ml).

Then, precisely measuring 0.2 ml, 0.4 ml, 0.6 ml, 0.8 ml, 1.0 ml and 1.2 ml of the reference solution, respectively placing the reference solution into 10 ml measuring flasks, respectively adding water to 3 ml, adding 2 ml acetic acid-sodium acetate buffer (pH4.5) and 2 ml 0.1 mol/L aluminum chloride solution, shaking well, adding 70% ethanol to the mark, and shaking well. The corresponding solution serves as the blank solution. The tests are performed according to ultraviolet-visible spectrophotometry (General Rules 0401 in Chinese Pharmacopoeia (2015 Edition) Volume IV). The absorbance is measured at 270 nm wavelength, and the standard curve is drawn with absorbance as ordinate and concentration as abscissa.

Taking 20 capsules of contents from the ginkgo biloba ketone ester capsule Sample 1# (prepared in Embodiment 2), the ginkgo biloba ketone ester capsule Control Samples 1* and 2* (prepared in Control Example 3), respectively mixing well, precisely weighing, grinding fine, and taking 0.2 g of powder. Precisely weighing the powder, placing the powder into Soxhlet extractors, adding 40 ml of 70% ethanol, heating in a water bath and refluxing for 4 hours, cooling, transferring the extract to 50 ml measuring flasks, diluting to the mark with 70% ethanol, and shaking well. Precisely measuring 0.5 ml into 10 ml measuring flasks, adding water to 3 ml, adding 2 ml acetic acid-sodium acetate buffer (pH4.5) and 2 ml 0.1 mol/L aluminum chloride solution, shaking well, adding 70% ethanol to the mark, and shaking well. The tests are performed according to ultraviolet-visible spectrophotometry (General Rules 0401 in Chinese Pharmacopoeia (2015 Edition) Volume IV). The absorbance is measured at 270 nm wavelength. The equivalent weight of rutin in the test product solution is read from the standard curve, which is calculated to obtain the content of total flavonoids.

The determination shows that the contents of total flavonoids in ginkgo biloba ketone ester capsule Sample 1# and ginkgo biloba ketone ester capsule Control Sample 1* are 21.31 mg/capsule and 16.88 mg/capsule respectively by using rutin ($C_{27}H_{30}O_{16}$) as a standard sample, which are within a specified data range of 14.08-26.40 mg/capsule. The content of flavonoids in ginkgo biloba ketone ester capsule Control Sample 2* is 11.77 mg/capsule by using rutin ($C_{27}H_{30}O_{16}$) as a standard sample, which is lower than the specified data range of 14.08-26.40 mg/capsule. Total flavonoids are active substances that contain free flavonoids besides total flavonoid glycosides. A certain amount of total flavonoids in ginkgo biloba ketone ester capsules endows ginkgo biloba ketone ester capsules with a good therapeutic effect. Therefore, the ginkgo biloba ketone ester capsule Control Sample 2* has a poor treatment effect. Ginkgo biloba ketone ester capsule Sample 1# and ginkgo biloba ketone ester capsule Control Sample 1* both have good therapeutic effects. However, the content of total flavonoids in ginkgo biloba ketone ester capsule Sample 1# is even higher, which is within a specified data range of 19.6-22 mg/capsule. Compared with ginkgo biloba ketone ester capsule Control Sample 1*, ginkgo biloba ketone ester capsule Sample 1# has a better therapeutic effect.

Embodiment 10

Taking 30 capsules of contents from the ginkgo biloba ketone ester capsule Sample 1# (prepared in Embodiment 2), the ginkgo biloba ketone ester capsule Control Samples 1* and 2* (prepared in Control Example 3), respectively mixing well, precisely weighing, grinding fine, and taking 2 g of powder. Precisely weighing the powder, placing the powder in a conical flask with stopper, precisely adding 10 ml of methanol, weighing, treating with ultrasonic (power: 180 W; frequency: 42 kHz) for 20 minutes, cooling, weighing again, using methanol to make up for the weight loss. Filtering, and taking the subsequent filtrate to obtain test product solutions D1, D2 and D3.

At the same time, taking appropriate amounts of ginkgolic acid C13:0 reference substance, ginkgolic acid C15:1 reference substance, and ginkgolic acid C17:1 reference substance, respectively, and precisely weighing the reference substances. The reference substances are added with methanol to prepare a series of mixed solutions respectively containing 0ng/ml, 10 ng/ml, 20 ng/ml, 50 ng/ml, 100 ng/ml and 200 ng/ml of each reference substance, so as to obtain the reference solutions.

Precisely pipetting 1 µl from the test product solutions D1, D2, D3 and the reference solution, respectively, then determining by high performance liquid chromatography-mass spectrometry (HPLC-MS) in General Rules 0512 and 0431 in Chinese Pharmacopoeia (2015 Edition) Volume IV. The conditions of the HPLC-MS are as follows: octadecylsilane chemically bonded silica gel serves as a filler; methanol-1% glacial acetic acid solution (90:10) serves as the mobile phase, eluting isostatically, fully cleaning with methanol-1% glacial acetic acid solution (99:1) that is at least 10 times the volume of the column after all the components to be determined have reached the peak; triple quadrupole mass spectrometer is used for multiple reaction monitoring (MRM) under electrospray ionization (ESI) negative ion mode. The monitoring ion pairs are shown in Table 3 below. If a chromatographic peak with the same retention time as that of the reference substance is detected in the test product solution, and the selected ion abundance ratio and the ion abundance ratio of the corresponding concentration of the reference solution meet the requirements of Table 4 below, the component can be determined to be present.

TABLE 3

| name | Parent ion | Quantitative ion pair | Qualitative ion pair |
|---|---|---|---|
| Ginkgolic acid C13:0 | 319.2 | 319.2→275.2 | 319.2→106.1 |
| Ginkgolic acid C15:1 | 345.2 | 345.2→301.2 | 345.2→119.0 |
| Ginkgolic acid C17:1 | 373.3 | 373.3→329.3 | 373.3→106.0 |

TABLE 4

| Relative ion abundance/% | >50 | 20~50 | 10~20 | <10 |
|---|---|---|---|---|
| Allowed relative deviation/% | ±20 | ±25 | ±30 | ±50 |

The determination shows that the contents of total ginkgolic acids in the ginkgo biloba ketone ester capsule Sample 1# and ginkgo biloba ketone ester capsule Control Sample 1* are 0.3 µg/capsule and 1.4 µg/capsule, respectively, which are both ≤2 µg/capsule. The content of total ginkgolic acids in the ginkgo biloba ketone ester capsule Control Sample 2* is 4.1 µg/capsule, which is greater than 2 µg/capsule. Ginkgolic acids have a sensitizing effect. Long-term administration of ginkgo preparation would cause accumulation of ginkgolic acids and do harm to the human body. Therefore, it is necessary to control the content of ginkgolic acids in ginkgo biloba ketone ester capsules, so as to keep the low content of ginkgolic acids in ginkgo biloba ketone ester capsules, prevent the use of high-ginkgolic-acid raw materials in the ginkgo biloba ketone ester capsules, and thus increase the safety of ginkgo biloba ketone ester capsules, which has never been controlled in traditional ginkgo biloba ketone ester capsules. The content of total ginkgolic acids in the ginkgo biloba ketone ester capsule Control Sample 2* exceeds the limit, which will cause harm to the human body. The contents of total ginkgolic acids in ginkgo biloba ketone ester capsule Sample 1# and ginkgo biloba ketone ester capsule Control Sample 1* are within the limit. However, ginkgo biloba ketone ester capsule Sample 1# has a lower content of total ginkgolic acids, which can reach ≤1 μg/capsule, and is less likely to cause sensitization and therefore has better safety.

Embodiment 11

Taking 30 capsules of contents from the ginkgo biloba ketone ester capsule Sample 1# (prepared in Embodiment 2), the ginkgo biloba ketone ester capsule Control Samples 1* and 2* (prepared in Control Example 3), respectively mixing well, precisely weighing, grinding fine, and taking 0.2 g of powder. Precisely weighing the powder, precisely adding 50 ml mixed solution of methanol-25% hydrochloric acid solution (4:1), weighing, placing in 85-90° C. water bath and heating at reflux for 30 minutes, taking out, cooling rapidly to room temperature, weighing again, using the above mixed solution to make up for the weight loss, and shaking well. Filtering, and taking the subsequent filtrate to obtain test product solutions E1, E2 and E3.

At the same time, taking appropriate amounts of quercetin reference substance, kaempferide reference substance and isorhamnetin reference substance, precisely weighing the reference substances. The reference substances are added with methanol to prepare mixed solutions respectively containing 30 μg, 30 μg, 20 μg of each reference substance per 1 ml, to obtain the reference solution.

Precisely pipetting 10 μl from the test product solutions and the reference solution, respectively, which are then determined by high performance liquid chromatography (HPLC) in General Rules 0512 in Chinese Pharmacopoeia (2015 Edition) Volume IV. The conditions of the high performance liquid chromatography are as follows: octadecylsilane chemically bonded silica gel serves as a filler; methanol-0.4% phosphoric acid solution (49:51) serves as the mobile phase; isocratic elution; the detection wavelength is 368 nm. The number of theoretical plates calculated by the quercetin peak is no less than 4000. The resolution between kaempferide peak and isorhamnetin peak should be greater than 1.5.

The content of total flavonol glycosides in the ginkgo biloba ketone ester is calculated according to formula (1): content of total flavonol glycosides=(quercetin content+kaempferide content+isorhamnetin content)×2.51.

The determination shows that the contents of total flavonol glycosides in ginkgo biloba ketone ester capsule Sample 1# and ginkgo biloba ketone ester capsule Control Sample 1* are 13.2 mg/capsule and 10.5 mg/capsule (calculated as dry products), respectively, which are within a specified data range of 9.6-14.0 mg/capsule. The content of total flavonol glycosides in ginkgo biloba ketone ester capsule Control Sample 2* is 6.7 mg/capsule (calculated as dry products), which is lower than the specified data range of 9.6-14.0 mg/capsule. Total flavonol glycosides are active substances that contain free flavonoids. A certain amount of total flavonol glycosides in ginkgo biloba ketone ester capsules endows ginkgo biloba ketone ester capsules with good therapeutic effect. Therefore, the ginkgo biloba ketone ester capsule Control Sample 2* has poor treatment effect. Ginkgo biloba ketone ester capsule Sample 1# and ginkgo biloba ketone ester capsule Control Sample 1* both have good therapeutic effects. However, the content of total flavonol glycosides in ginkgo biloba ketone ester capsule Sample 1# is even higher, which is within a specified data range of 12.0-14.0 mg/capsule. Compared with ginkgo biloba ketone ester capsule Control Sample 1*, ginkgo biloba ketone ester capsule Sample 1# has better therapeutic effect.

Precisely pipetting 10 μl from the test product solutions E1, E2, E3 and the reference solution, respectively, then determining by the above-mentioned high performance liquid chromatography (HPLC). The determination shows that in ginkgo biloba ketone ester capsule Sample 1# and ginkgo biloba ketone ester capsule Control Sample 1*, the chromatographic peak area ratios of quercetin to kaempferide are 0.88 and 0.97 respectively, which are within the specified data range of 0.8-1.2; the chromatographic peak area ratios of isorhamnetin to quercetin are 0.21 and 0.19 respectively, which are greater than 0.15; in ginkgo biloba ketone ester capsule Control Sample 2*, the chromatographic peak area ratio of quercetin to kaempferide is 0.55, lower than the specified data range of 0.8-1.2; the chromatographic peak area ratio of isorhamnetin to quercetin is 0.10, which is lower than 0.15. It can be seen from the above proportional relationship that there is no adulterated foreign substances in ginkgo biloba ketone ester capsule Sample 1# and ginkgo biloba ketone ester capsule Control Sample 1*, indicating the product process is normal, and the product quality is good. The quality of ginkgo biloba ketone ester capsule Control Sample 2* is poor due to the addition of quercetin and adulterated foreign substances.

Embodiment 12

Taking 20 capsules of contents from the ginkgo biloba ketone ester capsule Sample 1# (prepared in Embodiment 2), the ginkgo biloba ketone ester capsule Control Samples 1* and 2* (prepared in Control Example 3), respectively mixing well, precisely weighing, grinding fine, and taking 0.2 g of powder. Precisely weighing the powder, adding 10 ml of 75% methanol, treating with ultrasonic (power: 300 W, frequency: 50 KHz) for 10 minutes, centrifuging for 5 minutes (4000 rpm), taking the supernatant to obtain the test product solutions F1, F2 and F3.

At the same time, taking appropriate amounts of rutin reference substance, quercetin reference substance, kaempferide reference substance and isorhamnetin reference substance, precisely weighing the reference substances. The reference substances are added with 75% methanol to prepare a solution containing 30 μg of each reference substance per 1 ml, and the reference solution is obtained.

Precisely pipetting 10 μl from the test product solutions and the reference solution, respectively, which are then determined by high performance liquid chromatography (HPLC) in General Rules 0512 in Chinese Pharmacopoeia (2015 Edition) Volume IV. The conditions of the high-performance liquid chromatography are as follows: octadecylsilane chemically bonded silica gel serves as a filler (length of the column: 15 cm; inner diameter: 4.6 mm; particle size: 5 μm); acetonitrile serves as mobile phase A, and 0.1% formic acid solution serves as mobile phase B. Gradient elution is performed according to the specification in Table 5 below; the detection wavelength is 360 nm; the column temperature is 30° C.; the flow rate is 1.0 ml/min. The number of theoretical plates calculated by the rutin peak is no less than 10000.

TABLE 5

| Time (minutes) | Mobile phase A (%) | Mobile phase B (%) |
|---|---|---|
| 0-40 | 15-30 | 85-70 |
| 40-45 | 30-40 | 70-60 |
| 45-50 | 40 | 60 |
| 50-60 | 40-60 | 60-40 |
| 60-70 | 60 | 40 |

The similarity between the fingerprint spectra of test products and ginkgo biloba ketone ester capsule is calculated and compared according to "Similarity Evaluation System for Chromatographic Fingerprint of Traditional Chinese Medicine" (version 2.0). The fingerprint spectrum of the ginkgo biloba ketone ester capsule includes four common fingerprint peaks as shown in the drawing: peak 1 is the fingerprint peak of rutin, peak 6 is the fingerprint peak of quercetin, peak 7 is the fingerprint peak of kaempferide, and peak 8 is the fingerprint peak of isorhamnetin. The determination shows that the similarity between the fingerprint spectra of ginkgo biloba ketone ester capsule Sample 1# and ginkgo biloba ketone ester capsule Control Sample 1* and the chromatogram of the test product are 0.98 and 0.92, respectively, which are greater than or equal to 0.90. The similarity between the fingerprint spectrum of the ginkgo biloba ketone ester capsule Control Sample 2* and the chromatogram of the test product is 0.35, which is lower than 0.90. It can be seen from the above similarities that there are no adulterated foreign substances in ginkgo biloba ketone ester capsule Sample 1# and ginkgo biloba ketone ester capsule Control Sample 1*, indicating the product quality is good. The quality of ginkgo biloba ketone ester capsule Control Sample 2* is poor due to the addition of adulterated foreign substances.

Embodiment 13

Ginkgo biloba nursery leaves that serve as the medicinal raw materials in Embodiment 1 are selected and dried at 140-160° C. for 6-15 minutes, to serve as the raw material Sample 1; at the same time, conventional ginkgo biloba leaves that serve as the medicinal raw materials in Control Example 1 are selected to serve as the raw material Sample 2.

The contents of total flavonol glycosides and the chromatographic peak area ratios of flavonoid aglycones in raw material Sample 1 and raw material Sample 2 are determined according to the method described in Embodiment 9. The contents of terpene lactone in raw material Sample 1 and raw material Sample 2 are determined by the method described in Embodiment 4. The contents of total ash and acid-insoluble ash in raw material Sample 1 and raw material Sample 2 are determined according to the ash determination method described in General Rules 2302 in Chinese Pharmacopoeia (2015 Edition) Volume IV. The contents of extractum in raw material Sample 1 and raw material Sample 2 are determined according to the extractum determination method described in General Rules 2201 in Chinese Pharmacopoeia (2015 Edition) Volume IV. The contents of impurity in raw material Sample 1 and raw material Sample 2 are determined according to the impurity determination method described in General Rules 2301 in Chinese Pharmacopoeia (2015 Edition) Volume IV. The contents of water in raw material Sample 1 and raw material Sample 2 are determined according to the water determination method described in General Rules 0832 in Chinese Pharmacopoeia (2015 Edition) Volume IV. The contents of sulfur dioxide residue in raw material Sample 1 and raw material Sample 2 are determined according to the sulfur dioxide residue determination method described in General Rules 2331 in Chinese Pharmacopoeia (2015 Edition) Volume IV.

The determination shows that the contents of total flavonol glycosides in raw material Sample 1 and raw material Sample 2 are 1.63% and 0.63%, respectively. The content of total flavonol glycosides in raw material Sample 2, though meets the requirement of the Pharmacopoeia that the content of total flavonol glycosides is greater than or equal to 0.40%, does not meet the requirement specified in the present disclosure that the content of total flavonol glycosides is greater than or equal to 0.85%. The content of total flavonol glycosides in raw material Sample 1 is not only greater than or equal to 0.40%, but also greater than or equal to 0.85%. The raw material Sample 1 has a higher content of total flavonol glycosides, therefore has better raw material quality.

The determination shows that the contents of terpene lactones in raw material Sample 1 and raw material Sample 2 are 0.73% and 0.33%, respectively. The content of terpene lactones in raw material Sample 2, though meets the requirement of the Pharmacopoeia that the content of terpene lactones is greater than or equal to 0.25%, does not meet the requirement specified in the present disclosure that the content of terpene lactones is greater than or equal to 0.40%. The content of terpene lactones in raw material Sample 1 is not only greater than or equal to 0.25%, but also greater than or equal to 0.40%. The raw material Sample 1 has a higher content of terpene lactones, therefore has better raw material quality.

The determination shows that the chromatographic peak area ratios of quercetin to kaempferide in raw material Sample 1 and raw material Sample 2 are 0.99 and 0.46, respectively. Raw material Sample 1 meets the data range of 0.65-1.2 specified in the present disclosure, while raw material Sample 2 does not meet the data range of 0.65-1.2 specified in the present disclosure. The chromatographic peak area ratios of isorhamnetin to quercetin in raw material Sample 1 and raw material Sample 2 are 0.25 and 0.11, respectively. Raw material Sample 1 meets the requirement of >0.15 specified in the present disclosure, while raw material Sample 2 does not meet the requirement of >0.15 specified in the present disclosure. It can be seen from the above proportional relationship that as raw material, the quality of raw material Sample 1 is better than that of raw material Sample 2.

The determination shows that the contents of sulfur dioxide residues in raw material Sample 1 and raw material Sample 2 are 17 mg/kg and 99 mg/kg, respectively, which are both ≤150 mg/kg. The contents of sulfur dioxide residues in raw material Sample 1 and raw material Sample 2 are all within the limit. Therefore, the raw material qualities of raw material Sample 1 and raw material Sample 2 meet the requirements. However, raw material Sample 1 has better raw material quality due to its lower content of sulfur dioxide residue.

At the same time, the determination shows that the total ash content in raw material Sample 1 and raw material Sample 2 are 4.9% and 8.0%, respectively, which are both ≤10.0%. The acid-insoluble ash content in raw material Sample 1 and raw material Sample 2 are 0.89% and 1.76%, respectively, which are both ≤2.0%. The extractum content in raw material Sample 1 and raw material Sample 2 are 45.3% and 29.4%, respectively, which are both ≥25.0%. The impurity content in raw material Sample 1 and raw material Sample 2 are 0.78% and 1.64%, respectively, which are both ≤2.0%. The water content in raw material Sample 1 and raw material Sample 2 are 6.4% and 11.2%, respectively, which are both ≤12.0%. It can be seen that the above-mentioned contents in raw material Sample 1 and raw material Sample 2 are all within the specified limit range, and the quality of the raw materials meets the requirements. However, the relevant content indicators of raw material Sample 1 are better than that of raw material Sample 2. Therefore, the quality of raw material Sample 1 is better. Using the raw material Sample 1, it's possible to prepare ginkgo biloba ketone ester raw material samples with better quality can be prepared, thereby ginkgo biloba ketone ester capsule samples with better quality can be prepared.

In summary, the present disclosure provides a ginkgo biloba ketone ester capsule and a preparation method thereof. Through optimized preparation operations and conditions, a high-quality ginkgo biloba ketone ester capsule can be obtained. Compared with the ginkgo biloba ketone ester capsule prepared by traditional methods, the ginkgo biloba ketone ester capsule of the present disclosure has stable quality and a low unqualified rate. The consistency of different batches of ginkgo biloba ketone ester capsules is good. In particular, the ginkgo biloba ketone ester capsule can effectively control ginkgolic acids, preventing the use of high-ginkgolic-acid raw materials in the ginkgo biloba ketone ester capsules, so as to effectively improve the safety of ginkgo biloba ketone ester capsules. Therefore, the present disclosure effectively overcomes various shortcomings in the existing technology and has high industrial utilization value.

The above-mentioned embodiments are merely illustrative of the principle and effects of the present disclosure instead of limiting the present disclosure. Modifications or variations of the above-described embodiments may be made by those skilled in the art without departing from the spirit and scope of the disclosure. Therefore, all equivalent modifications or changes made by those who have common knowledge in the art without departing from the spirit and technical concept disclosed by the present disclosure shall be still covered by the claims of the present disclosure.

The invention claimed is:

1. A method for preparing a ginkgo biloba ketone ester capsule, comprising:
   mixing well a ginkgo biloba ketone ester raw material, dextrin, starch, low-substituted hydroxypropyl cellulose and carboxymethyl starch sodium according to a composition ratio, granulating, drying, adding magnesium stearate, mixing well, and filling into a capsule, to obtain the ginkgo biloba ketone ester capsule;
   wherein the composition ratio of the ginkgo biloba ketone ester capsule, in parts by weight, includes the following:
     35-45 parts of ginkgo biloba ketone ester raw materials;
     35-45 parts of dextrin;
     80-100 parts of starch;
     15-25 parts of low-substituted hydroxypropyl cellulose;
     6-10 parts of carboxymethyl starch sodium; and
     1-3 parts of magnesium stearate;
   wherein the preparation method of the ginkgo biloba ketone ester raw materials includes the following operations:

a) crushing ginkgo biloba leaves to obtain crushed ginkgo biloba leaves; adding 60% ethanol aqueous solution to the crushed ginkgo biloba leaves, extracting twice by heating at reflux and obtaining a first filtrate by filtration; adding water to the filtered residue left after the filtration, heating at reflux for extraction, and then obtaining a second filtrate by filtration; combining and concentrating the first filtrate and the second filtrate into a thick paste, dissolving in purified water, standing to cool, and filtering to obtain a filtrate;
   b) concentrating the filtrate and performing water-sedimentation, centrifuging the supernatant to obtain a centrifugal liquid; wherein the filtrate is concentrated to have no alcohol smell;
   c) loading the centrifugal liquid onto a macroporous resin column, then washing with water and eluting with solvent to obtain a first eluent; the first eluent includes a 50% ethanol eluent which is a high-concentration-solvent first eluent, and a combined solution of an 18% ethanol eluent and a 30% ethanol eluent which is a low-concentration-solvent first eluent;
   wherein the washing with water is forward-washing with purified water for 1.5 hours first, and then backwashing for 1 hour; the eluting with solvent is eluting with 18% ethanol aqueous solution, 30% ethanol aqueous solution and 50% ethanol aqueous solution in sequence to obtain 18% ethanol eluent, 30% ethanol eluent and 50% ethanol eluent, respectively;
   d) loading the low-concentration-solvent first eluent onto a polyamide column, then washing with water and eluting with ethanol to obtain a second eluent; wherein the low-concentration-solvent first eluent is concentrated to have no alcohol smell before being loaded onto the polyamide column, the washing with water is forward-washing by using purified water 0.5-2 times the volume of the polyamide column;
   e) combining and concentrating the second eluent with the high-concentration-solvent first eluent, and then extracting, drying, crushing, sieving, and mixing to obtain the ginkgo biloba ketone ester raw materials;
   wherein the ginkgo biloba ketone ester capsule, based on the loading weight of each capsule being 0.2 g, meets the following conditions:
     1) the content of rutin is less than or equal to 1.60 mg/capsule;
     2) the content of quercetin is less than or equal to 0.160 mg/capsule;
     3) the content of bilobalide is 1.04-2.08 mg/capsule;
     4) the content of ginkgolide J is 0.04-0.20 mg/capsule;
     5) the residual content of ethanol is less than or equal to 0.2 mg/capsule;
     6) the content of biflavonoids is less than or equal to 0.008 mg/capsule, the biflavonoids include amentoflavone, bilobetin, and ginkgetin; and
     7) the content of genistin is 0, and the content of ginkgolide M is 0.

2. The method for preparing the ginkgo biloba ketone ester capsule according to claim 1, comprising the following operations:
   A) according to the composition ratio, dividing the starch into a first part of starch and a second part of starch; preparing the second part of starch into a starch slurry, and then premixing the ginkgo biloba ketone ester raw materials, dextrin, the first part of starch, low-substituted hydroxypropyl cellulose and carboxymethyl starch sodium; granulating and drying after spraying the starch slurry;

B) sieving granules obtained by granulating and drying, adding magnesium stearate for mixing;

C) filling capsules with the granules obtained by mixing, to obtain the ginkgo biloba ketone ester capsule.

3. The method for preparing the ginkgo biloba ketone ester capsule according to claim 2, wherein operation A) includes one or more of the following:

A1) the starch is corn starch;

A2) the starch slurry is corn starch slurry, and the corn starch slurry is prepared by adding water to the second part of starch, stirring evenly and sieving;

A3) the time of the premixing is 10-12 minutes;

A4) when spraying the starch slurry, the premixture temperature is 54-56° C.;

A5) when granulating, the oscillation time is 110-130 seconds, and the oscillation frequency is 5-8 times within 110-130 seconds;

A6) stop drying when the temperature of the mixture after spraying the starch slurry is 60-64° C.;

A7) the time for the drying is 15-30 minutes.

4. The method for preparing the ginkgo biloba ketone ester capsule according to claim 2, wherein operation B) includes one or more of the following:

B1) the mesh number of the sieving is 14-18 mesh;

B2) the speed of the mixing is 20-25 rpm;

B3) the time for the mixing is 5-6 minutes.

5. The method for preparing the ginkgo biloba ketone ester capsule according to claim 1, wherein the preparation method of the ginkgo biloba ketone ester raw materials further includes the following operations:

b1) the relative density of the concentrated filtrate is 1.04-1.08; the water-sedimentation is interlayer cooling in 5-7° C. cooling water for 12-24 hours; the centrifugation conditions are as follows: the centrifugal speed is 13,000-15,000 rpm, and the centrifugal time per 3-5 L of supernatant is 0.75-1.25 min;

e1) the sieving is by passing through an 80-100 mesh sieve; the conditions for the mixing are: the mixing equipment is a total mixer; the mixing speed is 10-12 rpm; and the mixing time is 1.5-2.5 hours.

* * * * *